United States Patent [19]

Clark et al.

[11] 4,222,939

[45] Sep. 16, 1980

[54] PROCESS FOR PREPARING SOLID SODIUM AMOXYCILLIN

[75] Inventors: Dennis E. Clark, Basking Ridge; Robert C. Blyth, North Plainfield, both of N.J.

[73] Assignee: Beecham Group Limited, Great Britain

[21] Appl. No.: 937,735

[22] Filed: Aug. 29, 1978

Related U.S. Application Data

[63] Continuation of Ser. No. 810,500, Jun. 27, 1977, abandoned.

[30] Foreign Application Priority Data

Jul. 7, 1976 [GB] United Kingdom ............... 28179/76

[51] Int. Cl.² ........................................... C07D 499/68
[52] U.S. Cl. .................................. 260/239.1; 424/271
[58] Field of Search ...................... 260/239.1; 424/271

[56] References Cited

U.S. PATENT DOCUMENTS

| | | | |
|---|---|---|---|
| 3,674,776 | 7/1972 | Long et al. | .................... 260/239.1 |
| 4,029,804 | 6/1977 | Clark et al. | ....................... 424/271 |

OTHER PUBLICATIONS

Kirk-Othmer, "Encyclopedia of Chemical Technology", vol. 7, 2nd edition, pp. 368–369 (1965).
Remington's, "Pharmaceutical Sciences", 13th Ed. (1965), pp. 179–180.

*Primary Examiner*—Natalie Trousof
*Assistant Examiner*—Vera C. Clarke
*Attorney, Agent, or Firm*—Jacobs & Jacobs

[57] ABSTRACT

A process for making solid sodium amoxycillin is disclosed. The process comprises freeze drying a solution containing sodium amoxycillin in a solvent system containing water and a secondary or tertiary carbinol of four or five carbon atoms which is at least 5% w/v soluble in water at 25°.

19 Claims, No Drawings

PROCESS FOR PREPARING SOLID SODIUM AMOXYCILLIN

CROSS-REFERENCE

This is a continuation, of Ser. No. 810,500 filed June 27, 1977, now abandoned.

The present invention relates to an improved sodium amoxycillin and to a process for its preparation.

British Pat. No. 1,241,844 discloses inter alia amoxycillin and salts thereof. Amoxycillin which is the penicillin of the formula (I):

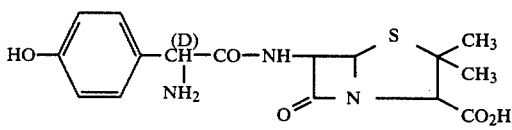

is widely recognized as having broad spectrum antibacterial activity of a high order. One of amoxycillin's great advantages is that it is very well absorbed after oral administration but there are occasions when it is desirable to administer it parenterally. It is possible to use the methods disclosed in British Pat. No. 1,241,844 to form for example the sodium salt of amoxycillin which may then be dissolved in sterile water and used as an injectable composition. However, the previously disclosed process for the preparation of the sodium salt tends to produce a product which contains up to about 10% of impurities. This disadvantage has not prevented use of the known sodium salt in forming injectable compositions of amoxycillin as the impurities have proved to be sufficiently non-toxic. However, it would clearly be of advantage if a process could be found that was able to provide a sodium amoxycillin which was of improved purity and which has good stability on storage. Such an improved sodium amoxycillin has now been prepared by a freeze drying process.

Accordingly the present invention provides a process for the preparation of a solid sodium amoxycillin which process comprises freeze drying a solution of sodium amoxycillin in a solvent system which contains water and a secondary or tertiary carbinol of 4 or 5 carbon atoms which is at least 5% w/v soluble in water at 25° C.

The solvent system used in the process of this invention will be a homogeneous mixture of the individual solvents. The secondary or tertiary carbinol will be present in any concentration from about 2% to about 60% (or to its maximum miscibility if lower).

The solvent system for use in the process of this invention will normally contain from 4% to 50% v/v of a secondary or tertiary carbinol. More suitably the solvent system will contain from 8% v/v to 35% v/v of a secondary or tertiary carbinol and preferably about 10% v/v to about 25% v/v of a secondary or tertiary carbinol. If desired a mixture of secondary or tertiary carbinols may be employed but this is normally less acceptable than using a single such compound.

The solvent system may also contain small amounts of other pharmaceutically acceptable solvents such as primary carbinols but in general it is preferable that such solvents are not present.

Suitable secondary or tertiary carbinols include sec-butanol, tert-butanol, 2-pentanol, 3-pentanol, 2-methylbutan-2-ol and the like.

Most suitably the carbinol used is a tertiary carbinol.

The preferred carbinol for use in this invention is tert-butanol. Use of tert-butanol as part of the solvent system has been found to give considerable and hitherto unpredictable advantages especially in terms of ease of operation of the process, the high purity and toxicological acceptability of the product, the low resulting solvent residues and the freedom from particulate matter on redissolution.

The concentration of sodium amoxycillin present in solution immediately prior to freezing is suitably in the range 8% w/v to 20% w/v, more suitably in the range 10% w/v to 15% w/v, for example, about 12% w/v.

The solution to be freeze dried may be prepared by any convenient method but it is believed that the most suitable method is by the addition of a solution of a sodium base to zwitterionic amoxycillin suspended in a mixture of water and a secondary or tertiary carbinol followed by any upward adjustment of volumes thought desirable.

The amoxycillin used is preferably amoxycillin trihydrate and the base is preferably sodium hydroxide although trisodium phosphate is also envisaged.

Normally the solution of the sodium base is added slowly until a clear solution is obtained. Care should be taken that a large excess of base is not added. Generally between 1 and 1.2 equivalents of the sodium base is employed, for example about 1.1. equivalents.

It is preferable that the temperature of the solutions is kept below 25° C. at all times to minimize decomposition. More suitably once addition of the base has begun the solutions are maintained at a temperature not substantially in excess of 20°.

Normally the solvents used have previously been rendered pyrogen free.

Once the solution of sodium amoxycillin has been prepared it should be cooled for use or for storage. Most suitably the solution is cooled to about 0° C. It is believed advisable to freeze dry the solution as soon as conveniently possible after it is prepared.

The freeze drying process may be carried out following standard procedures. The solution is frozen and the frozen material is subjected to low temperatures and pressures so that the solvent is removed without melting. In this present process, the frozen material is dried until a solid powder results containing not more than 10% by weight and preferably not more than 6% by weight of residual solvent.

The initial temperature at which evaporation is begun should be below $-25°$ C. most suitably below $-30°$ C. and preferably below $-35°$ C. The pressure will generally be reduced to less than $0.2\tau$.

The evaporation of solvents causes the solution to cool further, which slows the drying process. The evaporation may be accelerated by supplying heat and allowing the temperature of the frozen material to rise gradually. The rate at which heat is supplied and the temperature of the solution is allowed to rise must be such, that the no melting occurs. The rate at which the solution is heated is dependent upon the rate at which the solvent vapor is removed from above the frozen material. If the solvent vapor pressure, (i.e. the quantity of vapour) increases too much, then melting occurs. Thus, the rate of heating depends upon factors such as the vacuum which may be pulled above the solid and the surface area from which the solvent may escape etc., however, such factors are well known in the art and suitable heating rates are generally determined empirically. In the process of this invention, the final temperature at which drying is carried out does not normally exceed 60° C., and for preference the final drying temperature is not greater than 50° C. Generally we prefer to carry out this drying over a period of from 1 to 3 days.

An advantage of this process is that the solution to be freeze dried can be filled into open vials which are then placed in the freeze drier. Operation of the freeze drying process then produces solid sodium amoxycillin already in place in glass vials which may then be sealed. Such process is simple and convenient. The preceding process may easily be carried out under sterile conditions.

The solid produced by the freeze drying process of this invention appears to be particularly stable when it contains about 0.5-10% w/w of a secondary or tertiary carbinol, especially when it is tert-butanol.

The preceding powders may be dissolved in sterile water to provide an injectable composition of sodium amoxycillin, for human or veterinary use.

From the foregoing it will be realized that a preferred aspect of this invention provides a process for the preparation of solid sodium amoxycillin which process comprises freeze drying a solution of sodium amoxycillin dissolved in a mixture of water and tert-butanol.

A favored form of this aspect of the invention comprises freeze drying a solution consisting essentially of 10% w/v to 15% w/v of sodium amoxycillin dissolved in a solvent system consisting essentially of 2% v/v to 30% v/v of aqueous tert-butanol.

A further preferred aspect of this invention consists of solid powder which consists essentially of sodium amoxycillin and 0.5% w/w to 6% w/w of tert-butanol (and up to about 4% water).

An alternative view of this invention provides an injectable composition which comprises an aqueous solution of sodium amoxycillin which also contains tert-butanol present by from 0.5% to 6% of the weight of sodium amoxycillin.

Most suitably such compositions contain no more than 4% of the tert-butanol.

Those skilled in the art of freeze drying will realise that the solvent used in such processes is almost inevitable water. Although it is believed that aqueous ethanol has occasionally been used as a solvent for freeze drying it is believed that, prior to the present invention, no public recommendation or use of tert-butanol has occurred for preparing antibacterial agents such as a salt of penicillin or cephalosporin.

The following examples illustrate the invention:

EXAMPLE 1

Preparation of Solid Sodium Amoxycillin

Amoxycillin trihydrate (174 g) was suspended in a mixture of tert-butanol (100 ml) and water (500 ml). The suspension was maintained at 15° C. and neutralised to clarity by the addition of sodium hydroxide solution (2N, 230 ml). The resulting clear solution was filtered, made up to 1 l with water and cooled to 0° C. The cold solution was metered into glass vials, loaded onto the pre-cooled shelves of a freeze dryer, frozen and dried by the following cycle:

| Freezing | 6 hours |
| --- | --- |
| −45° C. with vacuum | 0-4 hours |
| −45° C. to +40° C. | 4-38 hours |
| 40° C. | 38-42 hours |

The resulting material assayed as containing 1-3% w/w tert-butanol and 1% w/w water in addition to the sodium amoxycillin.

EXAMPLE 2

Demonstration of Improvements (a) The purity of sodium salt produced by Example 1 was compared to that produced by the freeze drying process in the absence of tert-butanol and when the tert-butanol was replaced by ethanol. The results are given in Table 1.

TABLE 1

| Purity of Product | |
| --- | --- |
| Freeze Drying Solvent | % Purity of Resulting Sodium Amoxycillin (anhydrous basis) |
| Water | 85 |
| 15% v/v Ethanol/Water | 87 |
| 25% v/v Tert-butanol/Water | 95 |

(b) The storage stability of the sodium salt produced in Example 1 was compared to that produced by the freeze drying process in which the tert-butanol was replaced by ethanol. The results are given in Table 2.

TABLE 2

| | Stability of Product | |
| --- | --- | --- |
| | % Initial amoxycillin remaining after storage | |
| Freeze Drying Solvent | 12 weeks at 45° C. | 6 months at room temperature |
| 15% v/v Ethanol/ Water | 88 | 95 |
| 10% v/v Tert-butanol/ Water | 93 | 98 |

(c) The above data demonstrates that use of freeze drying from an tert-butanol/water solvent system produces a purer, more stable product that does freeze drying from a water or an ethanol/water solvent system.

EXAMPLE 3

Preparation of Bulk Freeze-Dried Sodium Amoxycillin

To a slurry of Amoxycillin Trihydrate (450 gms. activity) in water 1.7 L.) and tert-butanol (0.3 L.) at 22° C. was added 1.1. equivalents of 2N-sodium hydroxide. The resulting clear solution was immediately cooled to 0° C. and sterilely-filtered into freeze-drying trays to a depth of 0.95-1.0 cm. The trays were then loaded onto the pre-cooled shelves of a freeze-dryer, frozen to −50° C. and dried in a manner similar to that described in Example 1. The resulting Sodium Amoxycillin was 94.3% pure (anhydrous basis) and contained 1.2% w/w moisture and 0.9% w/w tert-butanol.

What we claim is:

1. A process for the preparation of solid sodium amoxycillin which comprises freeze drying a solution of sodium amoxycillin in a solvent system containing water and at least one secondary or tertiary $C_4$ or $C_5$ carbinol, which is at least 5% w/v soluble in water at 25° C.

2. A process according to claim 1 wherein the solvent system contains at least 2% of the carbinol.

3. A process according to claim 1 wherein the solvent system contains from 10% to 25% v/v of secondary or tertiary carbinol.

4. A process according to claim 1 wherein the carbinol is a tertiary carbinol.

5. A process according to claim 4 wherein the carbinol is tert-butanol.

6. A process according to claim 1 wherein the concentration of sodium amoxycillin in solution immediately prior to freeze drying is in the range of 8% w/v to 20% w/v.

7. A process according to claim 6 wherein the concentration of sodium amoxycillin is in the range of 10% w/v to 15% w/v.

8. A process according to claim 7 wherein the concentration of sodium amoxycillin is 12% w/v.

9. A process according to claim 1 wherein the freeze drying process is carried out at an initial temperature below $-25°$ C.

10. A process according to claim 9 wherein the initial temperature is below $-30°$ C.

11. A process according to claim 10 wherein the initial temperature is below $-35°$ C.

12. A process according to claim 1 wherein the initial temperature is allowed to rise gradually, such that no melting occurs, to a final drying temperature such that no more than 10% by weight of residual solvent remains in the solid product.

13. A process according to claim 12 wherein the final drying temperature is not greater than $50°$ C.

14. A process according to claim 12 wherein the product contains not more than 6% w/w of residual solvent.

15. A process according to claim 1 wherein the initial temperature is allowed to rise gradually over a period of at least one day to a final drying temperature which is not greater than $60°$ C. such that no more than 10% by weight of residual solvent remains in the solid product.

16. A process according to claim 1 wherein the solvents are pyrogen free.

17. A process according to claim 1 wherein the solution to be freeze dried is prepared by the addition of a sodium-base to zwitterionic amoxycillin trihydrate suspended in a mixture of the water and the carbinol.

18. A process for the preparation of solid sodium amoxycillin which comprises freeze drying a solution consisting essentially of 10% w/v of sodium amoxycillin dissolved in 2% v/v to 30% v/v of aqueous tert-butanol.

19. A process for the preparation of solid sodium amoxycillin of improved purity and stability having low solvent residue content and freedom from particulate matter upon redissolution which comprises freeze drying a frozen solution of sodium amoxycillin in water and a carbinol selected from the group consisting of sec-butanol, tert-butanol, 2-pentanol, 3-pentanol and 2-methylbutan-2-ol at low temperature and pressure to obtain a dried solid sodium amoxycillin in powder form containing not more than 10% by weight of residual solvent, the concentration of sodium amoxycillin in solution just prior to freezing being in the range of 8% w/v to 20% w/v and the carbinol being at least 5% w/v soluble in water at $25°$ C.

* * * * *